United States Patent [19]

Gupton

[11] Patent Number: 4,564,748
[45] Date of Patent: Jan. 14, 1986

[54] VARIABLE TEMPERATURE HEATING CONTROL SYSTEM FOR INHALATION THERAPY APPARATUS

[75] Inventor: John Gupton, Vernon Hills, Ill.

[73] Assignee: Respiratory Care, Inc., Arlington Heights, Ill.

[21] Appl. No.: 437,562

[22] Filed: Oct. 29, 1982

[51] Int. Cl.[4] .............................................. H05B 1/02
[52] U.S. Cl. .................................. 219/497; 219/330; 219/494; 219/506; 128/203.17; 128/203.27; 128/204.17
[58] Field of Search ............... 219/494, 497, 499, 501, 219/506, 508, 330, 272, 296–299, 302, 309, 275; 128/200.18, 203.17, 204.17, 203.27, 203.26, 204.14

[56] References Cited

U.S. PATENT DOCUMENTS

| | | | |
|---|---|---|---|
| 2,825,791 | 3/1958 | Jackson | 219/39 |
| 3,863,049 | 1/1975 | Hinman | 219/389 |
| 3,903,395 | 9/1975 | Hamstra | 219/497 |
| 3,903,883 | 9/1975 | Pecina et al. | 128/193 |
| 4,091,266 | 5/1978 | Ito et al. | 219/504 |
| 4,110,419 | 8/1978 | Miller | 219/275 |
| 4,161,172 | 7/1979 | Pickering | 128/1 B |
| 4,167,663 | 9/1979 | Granzow, Jr. et al. | 219/497 |
| 4,192,992 | 3/1980 | Stevens et al. | 219/494 |
| 4,201,204 | 5/1980 | Rinne et al. | 128/203.27 |
| 4,219,725 | 8/1980 | Groninger | 128/203.27 |
| 4,248,217 | 2/1981 | Brisson | 128/204.17 |
| 4,263,501 | 4/1981 | Wilhelmson | 219/494 |
| 4,300,037 | 11/1981 | Padder | 219/497 |
| 4,305,388 | 12/1981 | Brisson | 128/203.27 |
| 4,309,592 | 1/1982 | Le Boeuf | 219/497 |
| 4,322,594 | 3/1982 | Brisson | 219/497 |

Primary Examiner—M. H. Paschall
Attorney, Agent, or Firm—Allegretti, Newitt, Witcoff & McAndrews, Ltd.

[57] ABSTRACT

Operation of an inhalation therapy heater is regulated under control of the temperature sensor for the flow medium to maintain a selected temperature level to which the flow medium is heated during a warm-up period. Operation of the heater is intermittantly interrupted under control of a heater temperature sensor during the warm-up period to minimize temperature overshoot heating. A low temperature detector, disabled during the warm-up period, generates an alarm signal if the flow medium temperature remains below a lower limit at the end of the warm-up period.

17 Claims, 7 Drawing Figures

VARIABLE TEMPERATURE HEATING CONTROL SYSTEM FOR INHALATION THERAPY APPARATUS

BACKGROUND OF THE INVENTION

This invention relates to a control system for regulating the heating of water utilized to humidify oxygen gas being administered through an inhalation therapy apparatus.

The introduction of heat to humidified oxygen through inhalation therapy apparatus is generally well known as disclosed for example, in U.S. Pat. No. 3,903,883 to Pecina et al. The heating control system in such apparatus includes a temperature probe mounted in the inhalation tube, through which the humidified oxygen is conducted, to sense the temperature therein at a site adjacent entry into the patient, somewhat downstream of the heater location. The temperature measurement signal of the probe is fed to the heater control system in an effort to so regulate the amount of heat applied that the temperature of the humidified oxygen as it enters the patient is maintained constant at a manually selected level. Further, according to the Pecina et al patent a second temperature sensor is mounted on the heater block so as to monitor the heater temperature and through the control system prevent overheating of the heater.

Because of the spacing between the heater and the temperature probe site adjacent the patient, the flowing nature of the medium being heated, and the thermal inertia involved, a temperature stability problem arises for inhalation therapy apparatus of the foregoing type within the operating range of selected temperatures and variations in flow conditions anticipated. In particular, heating control systems heretofore effective to regulate heating so as to attain a desired selected temperature, would often overshoot the selected temperature and result in excessive temperature swing or "hunting". The extent of such temperature instability would of course vary dependent on variations in flow conditions of the humidified oxygen.

It is therefore an important object of the present invention to provide an improved heating control system for inhalation therapy apparatus wherein temperature instability and temperature overshoot heating is minimized despite anticipated flow condition variations.

A further object in association with the preceding object of the invention is to provide an improved heating control system through which a plurality of alarm conditions may be detected and heater shut-off automatically effected to avoid apparatus damage and patient injury.

The invention of the present matter has been found to be especially efficacious when used with a system as disclosed in issued U.S. Pat. No. 4,110,419 herein incorporated by reference. There is therein disclosed an ingenious cartridge humidifier. The patentee discloses an elongated generally cylindrical cartridge. It has a bottom cap and a top cap, both of which may be constructed of plastic. The two caps are joined by a cylindrical body portion which, to obtain good heat exchange properties, is constructed of a metal, such as aluminum. An electrical heater is provided which has a large bore therethrough into which the aforementioned cartridge is positioned and retained. Internally with respect to both the bottom cap and the cylindrical body portion cylindrical capillary active member is provided with a diameter sufficient to be in essential contact with the inner wall of the body portion whereby the capillary active member is in excellent heat exchange position with the heater. While the cartridge may be supplied with a fixed quantity of water for humidification it has been found to be particularly efficacious to supply water in a replenishable manner from a supply reservoir which may be an inverted bottle of water. The bottle and the heater may be suitably bracketed together whereby the entire thusly constructed unit may be suitably mounted. The bottom of the cartridge and the bottle containing a supply of water are fluidly connected by suitable egrees and ingress ports and a connecting tube to provide an inverted siphon to continuously supply water from the bottle to the cartridge as it is removed therefrom. The water in the cartridge wets the capillary active member to thereby provide a larger area for evaporating water than would be possible if the member were not present. The upper cap is provided with a concentrically located tube to which a conduit supplying oxygen or air under pressure is supplied. The said tube has a downwardly depending extension that extends concentrically into the mentioned body portion. The top cap is provided with an egress port which is located transverse to the axis of the cartridge. The port is connected to flexible conduit means which is designed to distribute the humidified gas to a patient. The egress port is in communication with an annular space around the mentioned downward extending tube of the upper cap. In this manner the gases are first directed downwardly through the said tube and then upwardly through the mentioned annular space to the egress port.

Other patents of interest in practicing the present invention are U.S. Pat. Nos. 4,172,105 and 4,195,044, which deal with further modifications and are also incorporated herein by reference.

SUMMARY OF THE INVENTION

In accordance with the present invention a variable temperature heating control system is provided for heated nebulization therapy apparatus having a flow medium temperature sensor in the inhalation tube adjacent the patient and an overheat temperature sensor on the heater block. The two sensors generally function to respectively regulate heating of the flow medium to a manually selected value adjacent the patient and to prevent overheating at the heater location. Additionally, the overheat sensor influences operation of a warm-up control through which the water is turned on and off in a cyclic manner as the rising temperature of the flowing medium approaches the manually selected value during a warm-up period. Heater cut-off is also effected in response to a plurality of alarm conditions detected by connections to the two sensors including a low temperature alarm condition sensed by a low temperature detector when the flow medium temperature remains below a lower limit at the end of the warm-up period during which the low temperature detector is disabled under control of a manually resettable disable circuit.

BRIEF DESCRIPTION OF DRAWING FIGURES

Other objects, advantages and novel features of the invention will become apparent from the following detailed description making reference to the accompanying drawings, wherein.

DETAILED DESCRIPTION OF PREFERRED EMBODIMENT

Figures 1, 3:
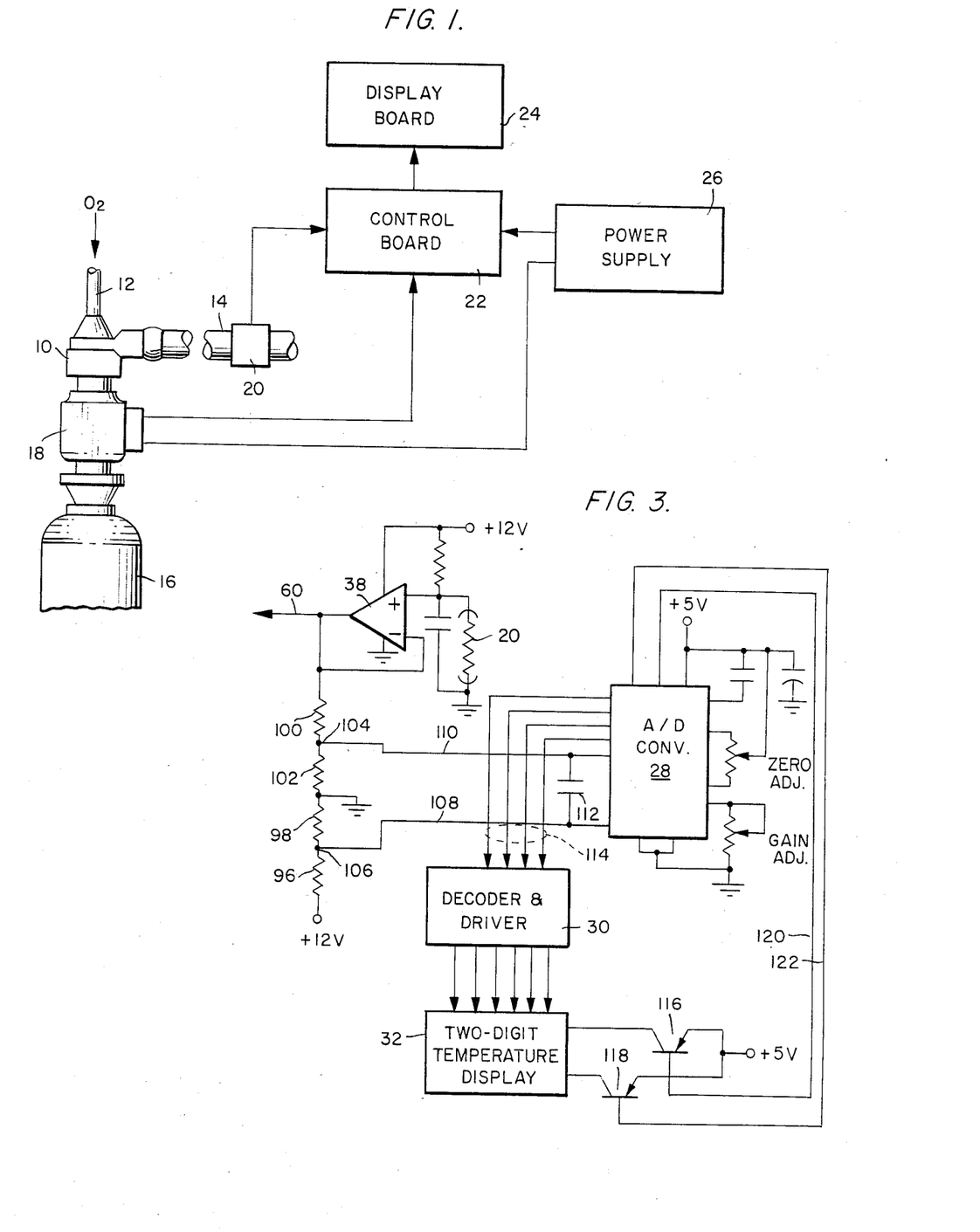
FIG. 1 is a simplified schematic illustration of the apparatus with which the present invention is associated.
FIGS. 3 through 7 are circuit diagrams illustrating the control system in greater detail.
Figure 2:
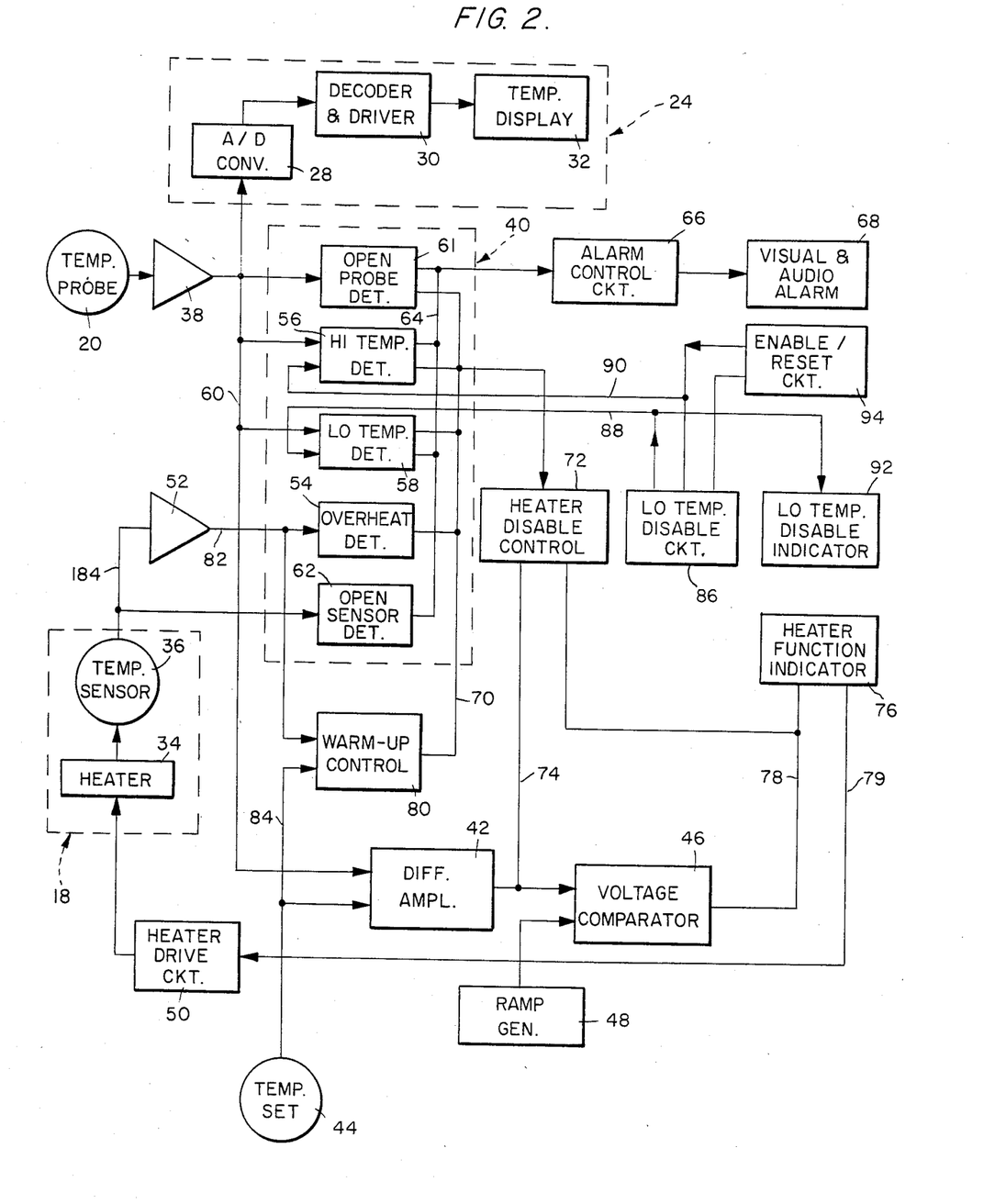
FIG. 2 is a block diagram illustrating the heating control system of the present invention for the apparatus shown in FIG. 1.

Referring now to the drawings in detail, FIG. 1 illustrates schematically a typical installation for the present invention, such as an inhalation therapy apparatus of the type shown in U.S. Pat. No. 3,903,883, including a nebulizer/humidifier 10 within which water is mixed with oxygen gas fed from a suitable source through tube 12 to supply humidified oxygen to a patient through an inhalation flow tube 14. The water is drawn up from a tank 16 through a column in a heater block assembly 18. In accordance with the present invention, heating of the water in heater assembly 18 is controlled by a temperature sensing probe 20 in the tube 14 adjacent to the patient and temperature sensor in the heater block assembly 18 in association with a heater control system which may be assembled from disconnectable modules such as a control board 22, a display board 24 and a power supply 26. As shown in FIG. 2, the display board 24 mounts an analog-to-digital converter 28, a decoder and driver component 30 and a two digit temperature display 32. The heater assembly 18 includes a block heater element 34 and an overheat sensor 36. Except for the temperature probe 20, the other components of the heater control system are mounted on the control board.

With continued reference to FIG. 2, the temperature probe 20, sensing the temperature of the humidified and heated oxygen gas in flow 14 just before entering the patient, feeds an analog temperature signal ($V_A$) through a buffer amplifier 38 to a detection circuit section 40, to the analog-to-digital converter 28 and to a differential amplifier section 42. The analog temperature signal is accordingly digitized in component 28 to drive the display 32 which visually registers the output temperature sensed by probe 20. In differential amplifier 42, the analog temperature signal level is reduced by an amount ($V_T$) selected through a temperature set circuit 44 to feed an error signal ($V_C$) to one input of a voltage comparator 46 having a second input to which a ramp voltage ($V_R$) is fed from a ramp voltage generator 48. Whenever the error signal level is equal to or greater than the ramp voltage, the voltage comparator produces a heater-on output ($V_O$) that is fed to a heater drive circuit 50 controlling energization of the heater element 34. The temperature of the heater element is sensed by a block mounted sensor 36 connected to a buffer amplifier 52 through which the heater temperature is monitored by an overheat detector 54 in the detection circuit section 40. The detection circuit section 40 also includes high and low temperature detectors 56 and 58 connected to the output of buffer amplifier 38 through temperature signal line 60 to receive an analog temperature input from probe 20. An open probe detector 61 is also connected to line 60 to detect open circuiting at probe 20. Open circuiting at sensor 36 is detected by another detector 62 in the detection circuit section directly connected to the output of sensor 36. The outputs of detectors 61, 56, 58, and 62 are connected by a common alarm signal line 64 through an alarm circuit 66 to a visual and audio alarm 68 in order to alert the operator to four different alarm conditions consisting of open circuiting at the sensors 20 and 36 and undesirable operation of the heater reflected by measurement of temperature at probe 20 either above an upper limit or below a lower limit. The alarm outputs of the detectors 61, 56 and 58 are also applied to a common disable signal line 70 to which the output of overheat detector 54 is also connected. Through a heater disable control 72 connected to line 70, a disable signal or signal shunt path is established in line 74 to interrupt drive of heater 34 by removal of any error signal input to comparator 46. Thus, under open circuit or extreme temperature conditions at probe 20 or overheat conditions at heater 34, cut off of the heater is effected. At the same time, a heater function indicator 76 is disabled by control 72, the indicator 76 being connected in series between the output of comparator 46 and the heater drive circuit 50 by lines 78 and 79 for otherwise signifying heater operation.

In accordance with the present invention, a warm-up control 80 is provided to generate a cyclic on-off signal applied to the disable signal line 70, through which heater cut off is effected as aforementioned in response to alarm conditions detected by detectors 61, 58, 56 and 54. The on-off heater signal is generated as a function of the heater temperature and the desired output temperature selected through the temperature set circuit 44. Thus, the warm-up control 80 receives a temperature input signal in line 82 derived from sensor 36 through buffer amplifier 52, and a temperature set voltage in line 84 also leading to the differential amplifier 42. The heater is thereby driven in an intermittent or cyclic mode during the warm-up period to prevent overshoot of the desired set temperature to which the humidified oxygen is being elevated under control of the temperature signal in line 60 and the set temperature voltage in line 84 through the differential amplifier 42, voltage comparator 46 and heater drive circuit 50.

A low temperature disable circuit 86 is provided as shown in FIG. 2 to establish an inhibit timing cycle during the warm-up period disabling the low temperature detector 58 through line 88. During such timing cycle, the high temperature detector 56 is enabled through reset signal line 90. At the end of the inhibit timing cycle, the detector 58 is enabled. If the rising temperature being monitored by probe 20 is still below the lower limit threshold of detector 58, a low temperature alarm signal is generated. The disable circuit 86 may be reset at any time through manual control 94 to initiate another inhibit timing cycle. The control 94 may also be actuated to enable the low temperature detector 58 during an inhibit timing cycle.

FIG. 3 shows in greater detail the circuitry of the display board module 24 in association with the temperature probe 20. A grounded thermister constituting the temperature sensing probe 20 in the humidified and heated oxygen tube 14 is connected to the non-inverting input of the buffer amplifier 38 as shown in FIG. 3. The amplifier has a feedback connection to its inverting input from the output thereof to which the temperature signal line 60 is connected. The line 60 feeds an analog signal voltage to a voltage dividing network formed by voltage reducing resistors 100 and 102 connected in series between ground. Also, series resistors 96 and 98 are connected between ground and the +12 volt output of the power supply. The junctures 104 and 106 between each pair of resistors are connected to input voltage lines 108 and 110 across which capacitor 112 is connected to supply an analog input signal to the analog-to-digital converter 28. The analog input is thereby converted to a coded digital output transmitted through four data bus lines 114 to the decoder and driver component 30 from which the two digit display 32 is driven. Thus, the display 32 is operative to continuously indicate the output temperature in terms of degrees centigrade. The display 32 is energized by the +5 volt output of the power supply through two transistors 116 and 118 switched on in synchronization with the converter through lines 120 and 122.

Figure 4:
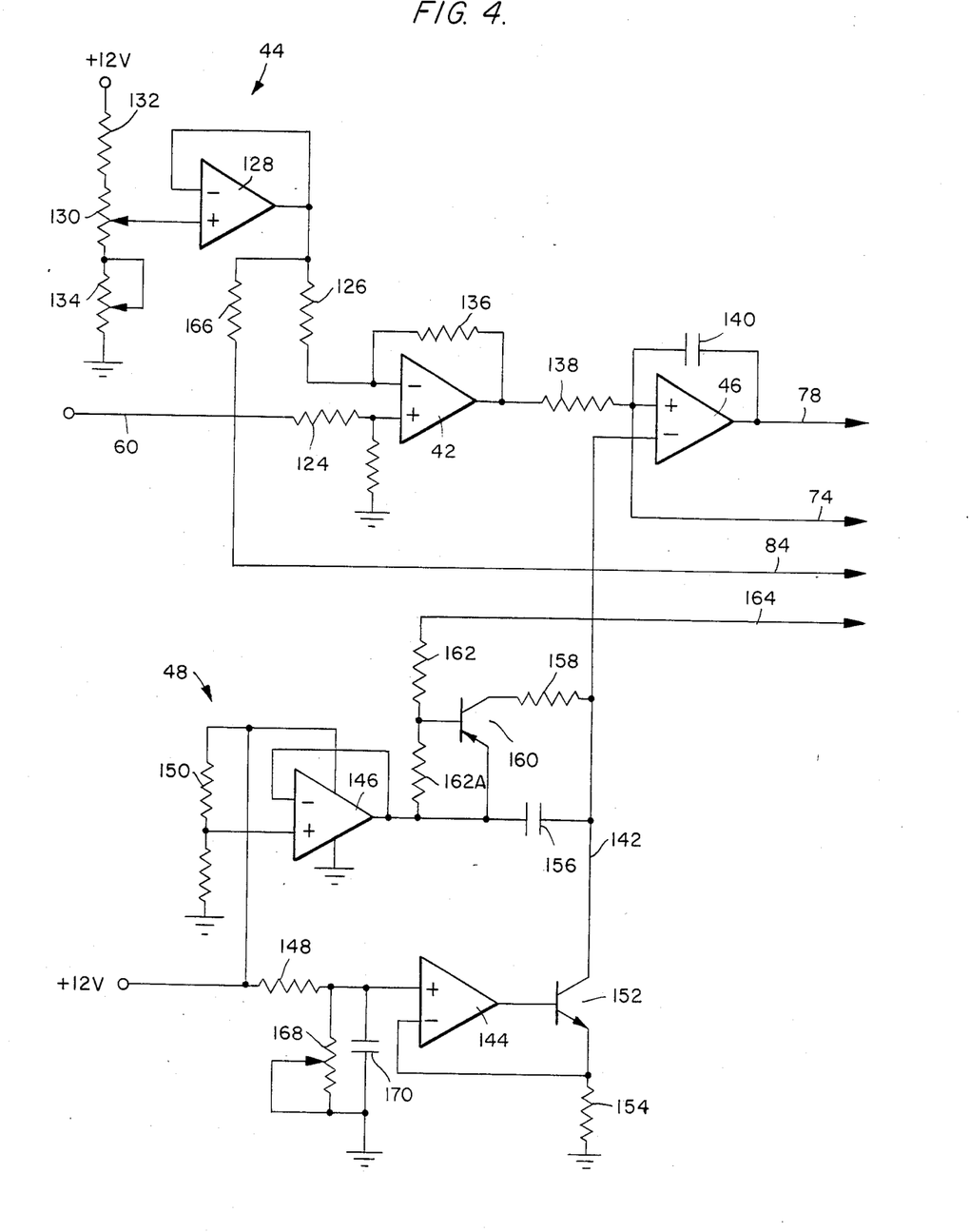

As shown in FIG. 4, the analog temperature signal ($V_A$) in line 60 is also fed through resistor 124 to the non-inverting input of the differential amplifier 42 having an inverting input through which temperature adjustment may be effected by an operator for different flow conditions through the temperature set circuit 44. A resistor 126 couples the output of amplifier 128 in the temperature set circuit to the inverting input of the differential amplifier 42. The output of amplifier 128 is proportional to its non-inverting input from the operator settable resistor 130 connected in series with resistors 132 and 134 between the +12 volt source and ground. Thus, an operator selected voltage signal ($V_T$) is applied to the differential amplifier 42 to produce an error voltage ($V_C$) at its output connected by feedback resistor 136 to the inverting input. The error voltage signal ($V_C$) is applied through coupling resistor 138 to the non-inverting input of the voltage comparator amplifier 46 having an output coupled by feedback capacitor 140 to the non-inverting input. The inverting input of comparator amplifier 46 receives a ramp voltage signal ($V_R$) from the ramp voltage generator 48 through ramp voltage signal line 142. The ramp generator includes amplifiers 144 and 146 having non-inverting inputs respectively coupled by voltage reducing resistors 148 and 150 to the +12 volt source with feedback connections to the inverting inputs. The output of amplifier 144 is applied to the base of transistor 152 causing it to conduct a negative going signal current at an adjusted level in the ramp voltage signal line 142 connected to ground through resistor 154. This signal current is also fed back to the inverting input of amplifier 144. The voltage output of amplifier 146 is applied to the ramp voltage signal line 142 through capacitor 156 in parallel with resistor 158 when transistor 160 is switched on by a negative voltage signal applied to its base through a resistor 162 connected to a zero voltage detection line 164.

The differential amplifier 42 receives the temperature set signal ($V_T$) in line 84 from the temperature set circuit 44 through resistor 166 while the output signal ($V_O$) from comparator 46 is fed through line 78 to drive circuit 50 only when the error voltage input ($V_C$) is equal to or greater than the ramp voltage ($V_R$). The ramp voltage level may be adjusted through ground resistor 168 connected to the non-inverting input of amplifier 144 in parallel with grounded capacitor 170. The detection circuit section 40 receives an input from the temperature signal line 60 to provide the various condition alarm signals. The signal disabling line 74 is connected to the non-inverting input of voltage comparator 46 to shunt the error signal applied thereto for heater shut off purposes as aforementioned.

Figure 5:
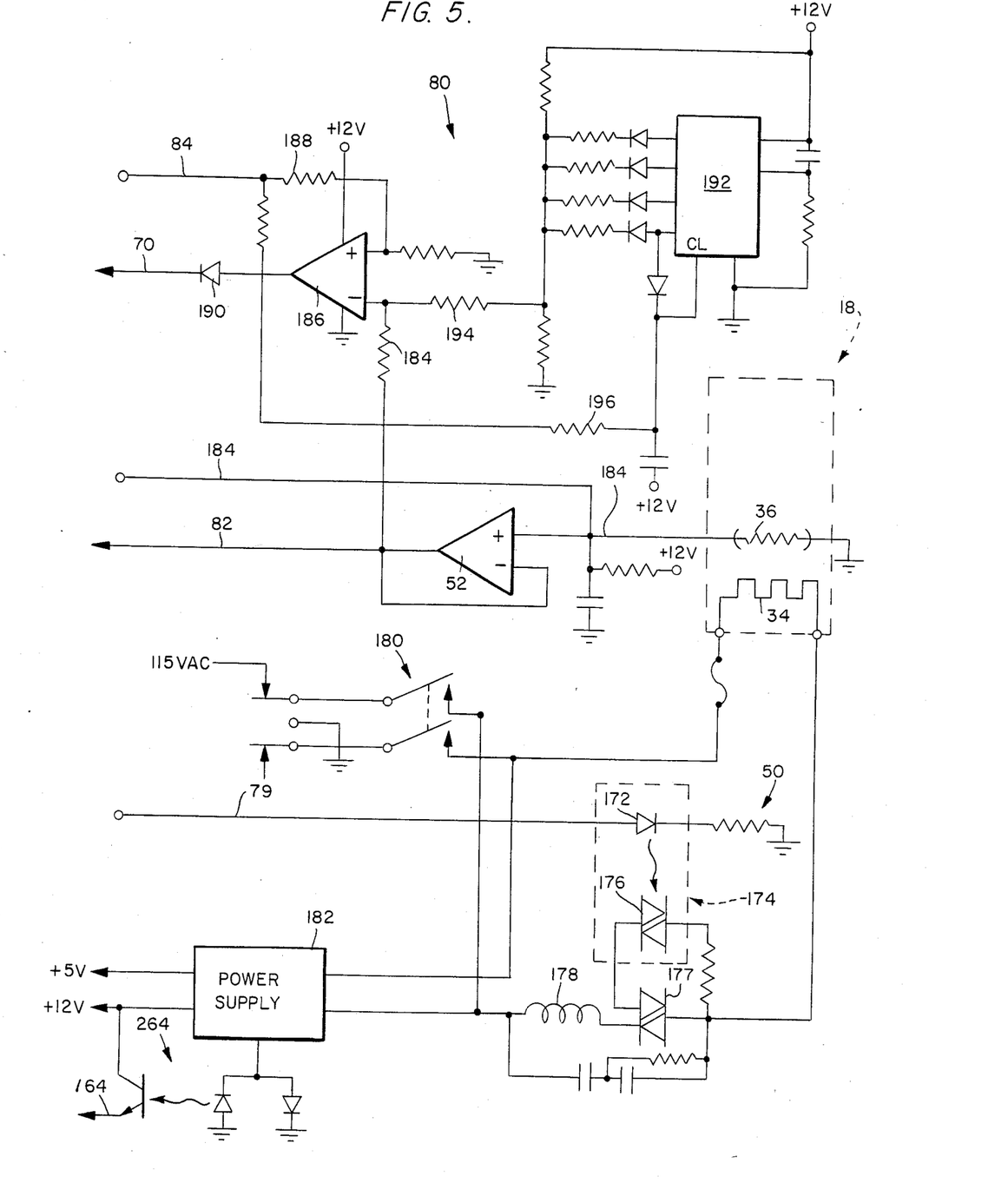

The heater warm-up control 80 as diagrammed in FIG. 5 controls energization of the heater element 34 in the heater block 18 within which thermistor sensor 36 is mounted. An output signal ($V_O$) from the comparator 46 in line 78 is applied to indicator 76 and subsequently is applied in line 79 to the light emitting diode 172 of the opto-coupling 174 in the heater drive circuit 50 to switch on the triac 176, 177 through its gate electrode. The triac is connected in series with an inductor 178 and to one of the terminals of the heater element 34, and is connected to the power switch 180 to which the other fused terminal of the heater element is connected. The power switch is connected to a 115 VAC power source. Thus, with the power switch closed the heater drive circuit 50 will energize the heater element in response to a signal voltage ($V_O$) in line 178. The 115 VAC source is also continuously applied to the power supply 182 upon closing of power switch 180 to establish the +12 volt and +5 power source.

The temperature of the heater block 18 is sensed by the thermistor type sensor 36 to apply a temperature voltage signal through line 184 to the non-inverting input of the buffer amplifier 52 from which an amplified temperature signal is fed by line 82 to the detection section 40 and through resistor 184 to the inverting input of amplifier 186 in the heater warm-up control 80. The temperature set signal ($V_T$) in line 84 is applied through resistor 188 to the non-inverting input of amplifier 186. A control signal output of the amplifier is applied through diode 190 to the disable control line 70. The control signal output of amplifier 186 will be determined by the input from the temperature set circuit applied to its non-inverting input and inputs applied from buffer amplifier 52 through resistor 184 and from a temperature limit control circuit 192 coupled by resistor 194 to the inverting input of amplifier 186. Resistor 196 connects the output of amplifier 186 to the control circuit 192 as shown in FIG. 5 to clock its operation in supplying a reference voltage to amplifier 186 for on-off cycling control of the heater through disable control line 70. The control circuit 192 thereby functions to gradually raise the temperature limits of the heater block after every two on/off cycles of the heater.

Figure 6:
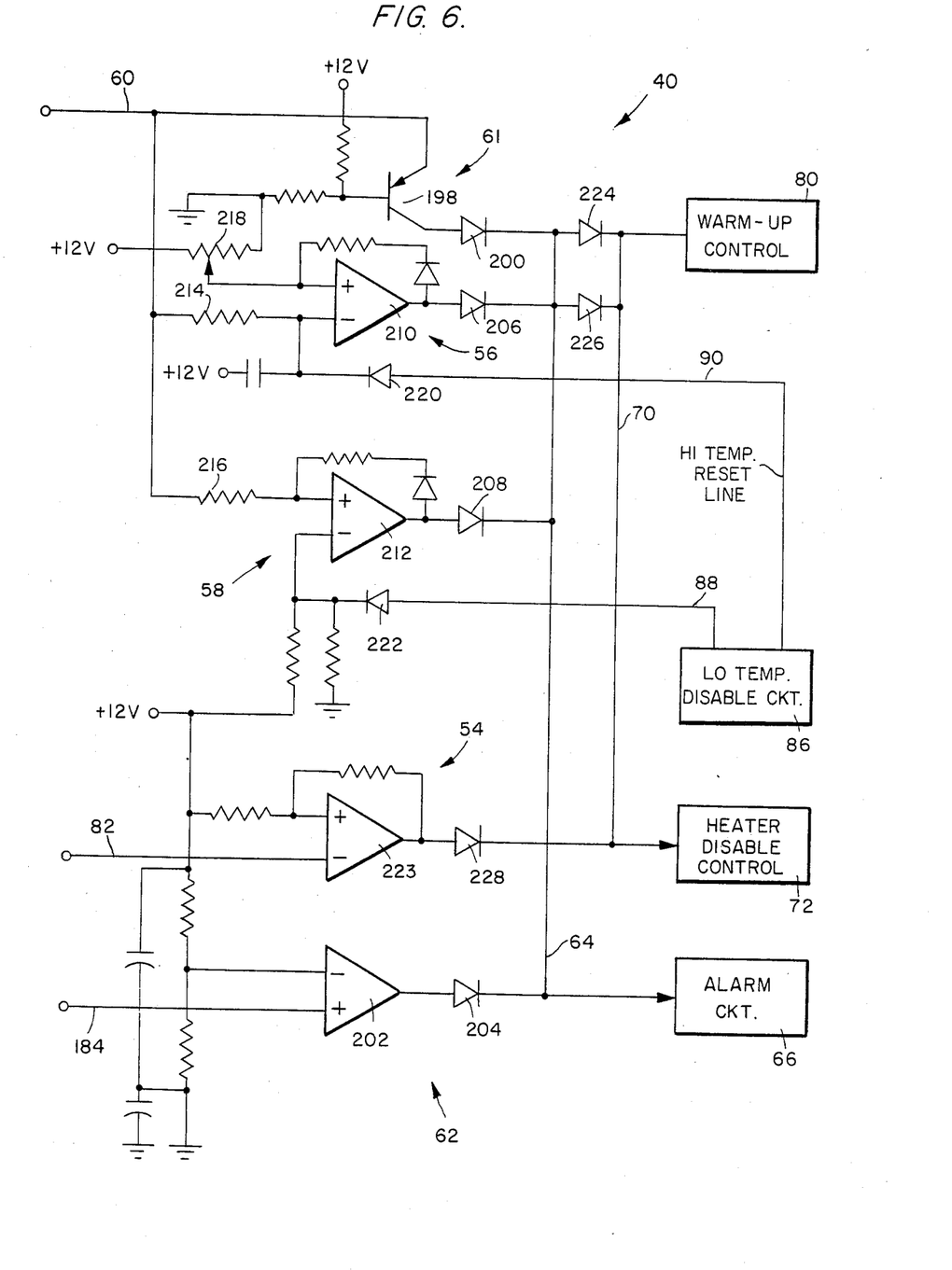
Figure 7:
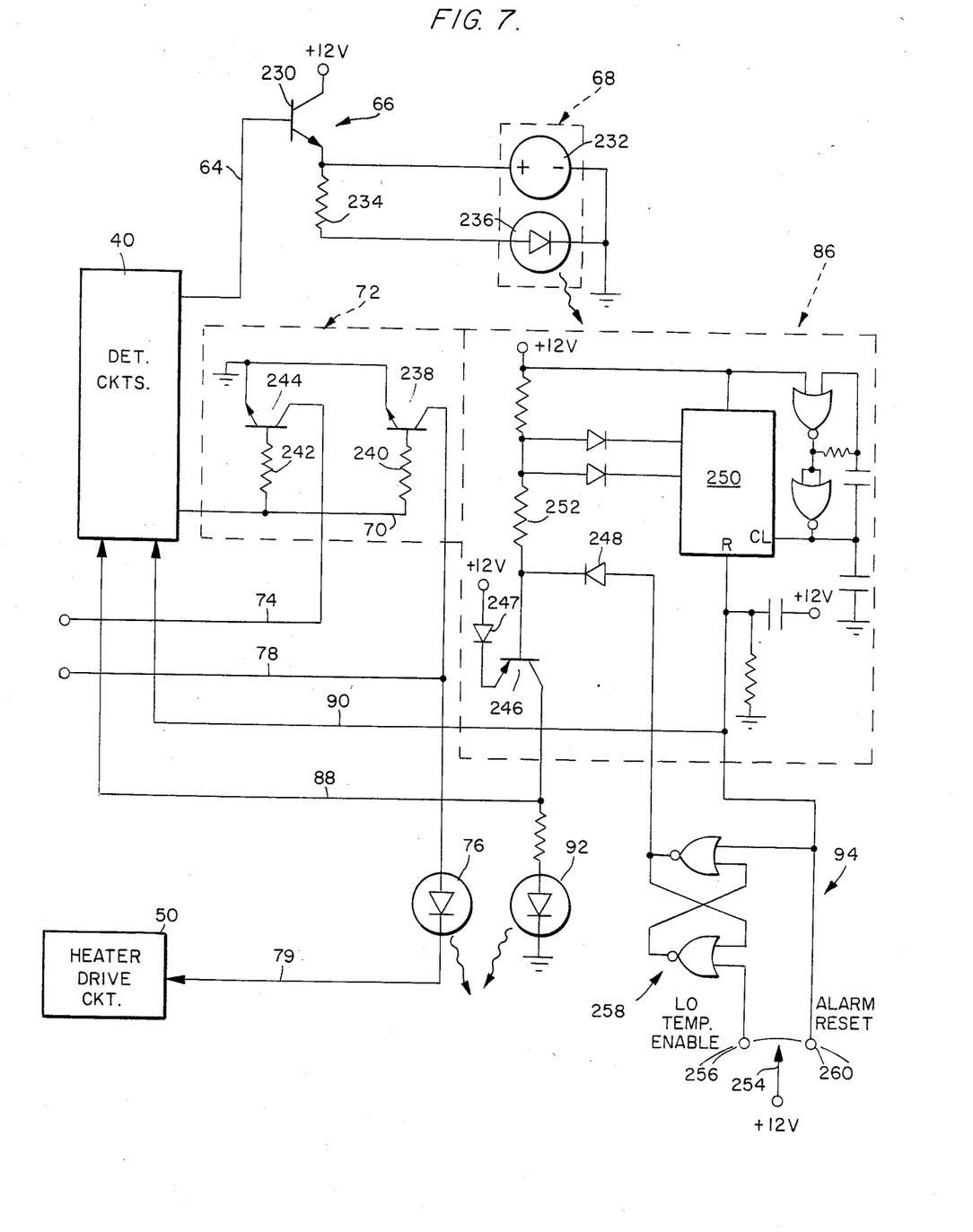

Referring now to the detection circuit section 40 shown in FIG. 6, the temperature signal from sensor 20 in line 60 is applied in parallel to open probe detector 61, high temperature detector 56 and low temperature detector 58. The open probe dectector includes a transistor 198 through which temperature signal current is conducted by diode 200 to alarm signal line 64. The signal from the other sensor 36 in the heater block applied to line 184 is amplified by the open sensor detection amplifier 202, the output of which is also applied to the alarm signal line 64 through diode 204. Other output signals are applied to this alarm signal line 64 through diodes 206 and 208 by the amplifiers 210 and 212 of the detectors 56 and 58. The temperature signal line 60 is coupled by resistor 214 to the inverting input of the high temperature detection amplifier 210 while resistor 216 couples line 60 to the non-inverting input of the low temperature detection amplifier 212. Both of the latter amplifiers have series connected, feedback resistor and diode arrangements with an adjustable resistor control 218 for the amplifier 210. The output alarm signals applied to signal line 64 are fed to the alarm circuit 66. From the low temperature disable circuit 86 disabling and reset signals (via enable/reset circuit 94 as shown in FIG. 7) are fed back through diodes 222 and 220, respectively, to the inverting inputs of the detection amplifiers 212 and 210 by lines 88 and 90, respectively. The signal outputs of the detectors 61 and 56 and overheat detection amplifier 223 are connected in parallel through diodes 224, 226 and 228 to the common disable control line 70 connected to the heater disable control 72 and to the output amplifier 186 in the warm-up control 80.

FIG. 7 illustrates the alarm circuit 66 to which the alarm signals are fed through line 64 connected to the base of a transistor 230. When switched on by an alarm signal, transistor 230 conducts energizing current to audio alarm device 232 and through resistor 234 to a visual LED type alarm device 236 forming the alarm section 68. A visual LED type function indicator 76 on the other hand is illuminated to signify heater operation. Toward that end a signal ($V_O$) in line 78 is applied to indicator 76 for energization thereof unless the signal is shunted to ground by transistor 238 of the disable control 72 held non-conductive by an enable signal in line 70 from the dectection section 40 connected by resistor 240 to the base of transistor 238. The disable control line 70 is also connected by resistor 242 to the base of transistor 244 in order to similarly control shunting of the output error signal ($V_C$) from differential amplifier 42 through line 74. Thus, open probe and extreme temperature conditions not only produce an alarm but disable heater operation and extinguish its function indicator 76. A low temperature alarm, when enabled, will also turn off the heater.

The other function indicator 92 as shown in FIG. 7 is energized through transistor 246 connected in series with diode 247 to signify that the low temperature detector 58 is disabled. Toward that end, transistor 246 is switched on by a negative bias applied to its base through resistor 252. When switched on, the transistor 246 applies a positive signal through line 88 and diode 222 to the inverting input of amplifier 212 so as to disable the low temperature detector 58. The control signal in line 88 is generated under control of a timer circuit 250 in disable circuit 86 and the manually operable control 94.

When power is initially turned on, the +12 volts applied to timer circuit 250 initiates an inhibit timing cycle at the end of which a positive voltage signal is applied through resistor 252 to the base of transistor 246, causing it to switch off. If the output temperature sensed by thermistor 20 has failed to rise above the lower limit at that time, it will be detected and alarm devices 232 and 236 energized through transistor 66 as aforementioned. This low temperature operation of the alarm section 68 will be identified by the preceding energization of low temperature disable indicator 92 through the transistor 246 during the inhibit timing cycle. The disabling current in line 88 fed to the low temperature detection circuit during the inhibit timing cycle may be instantly terminated if desired by turning switch 254, in control 94, to the low temperature enable position engaging contact 256 connected to gate circuit 258 and diode 248 to the base of transistor 246 causing it to switch off. In this fashion, the low temperature detection circuit 58 is enabled before the end of the inhibit timing cycle to see if the lower temperature limit has been prematurely surpassed. The inhibit timing cycle may be initiated at any time after power turn on by toggling switch 254 to the reset position engaging reset contact 260 connected to the gate circuit 258 and to the reset terminal of the timing circuit 250. Such reset will again energize indicator 92 through transistor 246 for the duration of the timing cycle.

When the output temperature sensed by thermister 20 exceeds the upper limit established in the high temperature detection circuit 56, the output signal applied to signal line 64 energizes the alarm devices 232 and 236 through transistor 230 as aforementioned. At the same time a disable signal in disable control line 70 is applied through resistors 240 and 242 to the bases of transistors 238 and 244 as shown in FIG. 7, causing shut off of the heater through line 74 and extinction of indicator 76. The inverting input of high temperature detection amplifier 210 is connected by reset signal line 90 to the reset contact 260 so that reset operation of switch 254 will disable the low temperature detection circuit 58 and resume heater energization provided the output temperature is under the upper limit established by the high temperature detector 56.

An opto-coupler circuit 264 connected to power supply 182 as shown in FIG. 5 generates a precise ramp signal applied to voltage signal line 164 connected by resistor 162 to the base of transistor 160 as shown in FIG. 4. A reset signal is thereby applied through transistor 160 to the ramp voltage generator 48.

The temperature sensor 20 is operative through the control system herein before described to provide optimum temperature stability under a variety of anticipated flow conditions including ventilated and nonventilated flow within a useful flow rate range such as five to thirty liters per minute (LPM). The temperature stability is characterized in one embodiment of the invention by a relatively small deviation of two degrees centigrade in output temperature from a desired temperature established through the temperature set circuit 44 after an initial warm-up period to which the timer circuit 250 is set, assuming the flow rate of the humidified oxygen in tube 14 is within the operative range aforementioned. Should the output temperature sensed by probe 20 exceed an upper limit to which the high temperature detector 56 is adjusted (between 39.6° C. and 40.6° C.), an alarm condition occurs to energize the alarm section 68 and cause shut-down of the heater 34 until the output temperature has decreased below a trip point with switch 254 manually displaced to the reset position. The low temperature detector 58 which is disabled during the inhibit timing cycle of timer 250, is enabled by toggling of switch 254 to the low temperature enable position engaging contact 256. The alarm inhibit time delay is also effected when power is initially turned on. Such low temperature alarm operation will enable one to guard against a thermal runaway condition that would occur if the sensor 20 is dislodged from its position in tube 14.

Alarm conditions are also produced in the control system by opening circuiting at the sensors 20 and 36. Open circuit at probe 20 will be occasioned by a low or zero reading of display 32. All alarm conditions cause shut off of the heater 34 and extinguish the heater function indicator 76.

Overshoot heating by heater 34 above the desired temperature is minimized by the heater warm-up control 80 in accordance with the setting of the temperature set circuit 44 so that the heater 34 will cycle on and off as the desired temperature is approached during the warm-up period.

What is claimed is:

1. A heating control system comprising, in combination:

heater means for heating a flowing gas, said heater means including a heater block;

temperature sensor means, downstream of said heater means, for sensing the temperature of said flowing gas and providing a sensor signal related thereto;

temperature probe means for sensing the temperature of said heater block and providing a probe signal related thereto;

set means for selecting a desired temperature for said flowing gas and providing a set signal related thereto;

control means, responsive and interconnected to said temperature sensor means, said temperature probe means, and said set means, for controlling the operation of said heater means; and display means for displaying the temperature of said flowing gas as sensed by said temperature sensor means downstream of said heater means;

said control means defining a high temperature limit and a low temperature limit so as to establish a permissible temperature range, said control means disabling said heater means whenever said sensor signal indicates that the temperature of said flowing gas is outside said permissible temperature range;

said control means defining a block temperature limit and disabling said heater means whenever said probe signal indicates that the temperature of said heater block exceeds said block temperature limit so as to substantially avoid a runaway condition;

said control means monitoring said sensor signal and said set signal and enabling said heater means in a predetermined manner whenever said sensor signal indicates that the temperature of said flowing gas is below said desired temperature;

said control means including warm-up means for intermittently enabling and disabling said heater means to substantially avoid overshooting said desired temperature for said flowing gas, said warm-up means being interconnected with and responsive to said set means and said temperature probe means, said warm-up means including a predetermined warm-up limit based upon said desired temperature of said set means, said warm-up means becoming operative when said probe signal indicates that the temperature of said heater block exceeds said warm-up limit.

2. A heating control system as claimed in claim 1 wherein said control means includes differential amplifier means for receiving said set signal and said sensor signal and providing an error signal in response thereto.

3. A heating control system as claimed in claim 2 wherein said control means further includes ramp means for generating a ramp signal and comparator means for receiving and comparing said error signal and said ramp signal, said comparator means providing a heater-on signal whenever a predetermined relationship exists between said error signal and said ramp signal.

4. A heating control system as claimed in claim 3 wherein said control means shunts said error signal to disable said heater means.

5. A heating control system as claimed in claim 1 wherein said control means includes low temperature disable means for inhibiting any disablement of said heater means based upon said low temperature limit during a predetermined timing cycle.

6. A heating control system as claimed in claim 5 wherein said low temperature disable means includes timing means for clocking said predetermined timing cycle.

7. A heating control system as claimed in claim 6 wherein said control means

8. A heating control system as claimed in claim 1 wherein said warm-up means includes control circuit means for providing an incrementally increasing control signal and amplifier means for receiving said probe signal and said incrementally increasing control voltage and for responsively producing an enable/disable signal.

9. A heating control system as claimed in claim 1 wherein said control means further includes sensor means for monitoring the operating condition of said temperature sensor means and said temperature probe means, respectively.

10. A heating control system as claimed in claim 1 wherein said heater means is adapted to receive in heat-transfer relationship a column member.

11. A heating system as claimed in claim 10 where said column member is operatively interconnected to a supply of a liquid, said supply controllably providing said liquid to said column member.

12. A heating control system as claimed in claim 1 further comprising alarm means, responsive and interconnected to said control means, for indicating the operational state of said system.

13. A heating control system as claimed in claims 1, 5, or 12 wherein said control means further includes reset means for operatively resetting and re-initiating said control means, said control means continuing disablement of said heater means until said reset means is actuated.

14. A system for controllably heating a flowing gas comprising, in combination:

a humidifying cartridge;

means for passing a gas through said humidifying cartridge to provide said flowing gas;

heater means for receiving said humidifying cartridge and for heating said flowing gas;

temperature sensor means, downstream of said heater means, for sensing the temperature of said flowing gas and providing a sensor signal related thereto;

temperature probe means for sensing the temperature of said heater means and providing a probe signal related thereto;

set means for selecting a desired temperature for said flowing gas and providing a set signal related thereto;

control means, responsive and interconnected to said temperature sensor means, said temperature probe means, and said set means, for controlling the operation of said heater means;

display means for displaying the temperature of said flowing gas as sensed by said temperature sensor means downstream of said heater means; and alarm means, responsive and interconnected to said control means, for displaying a series of operating conditions within said system;

said control means defining a high temperature limit and a low temperature limit so as to establish a permissible temperature range, said control means disabling said heater means whenever said sensor signal indicates that the temperature of said flowing gas is outside said permissible temperature range;

said control means defining a block temperature limit and disabling said heater means whenever said probe signal indicates that the temperature of said heater means exceeds said block temperature limit so as to substantially avoid a runaway condition; said control means monitoring said sensor signal and said set signal and enabling said heater means in a predetermined manner whenever said sensor signal indicates that the temperature of said flowing gas is below said desired temperature;

said control means including warm-up means for intermittently enabling and disabling said heater means to substantially avoid overshooting said desired temperature for said flowing gas, said warm-up means being interconnected with and responsive to said set means and said temperature probe means, said warm-up means including a predetermined warm-up limit based upon said desired temperature of said set means, said warm-up means becoming operative when said probe signal indicates that the temperature of said heater block exceeds said warm-up limit.

15. A system as claimed in claim 14 wherein said alarm means provides an indicator whenever the temperature of said flowing gas is outside said permissible range and whenever said heater means is enabled by said control means.

16. A system as claimed in claim 14 wherein said control means includes low temperature disable means for inhibiting disablement of said heater means whenever said low temperature limit is violated during a predetermined cycle time following activation of said system.

17. A system as claimed in claim 14 wherein said control means includes reset means for re-initiating said system, any disablement of said heater means by said control means being continuous until operation of said system is re-initiated through said reset means.

* * * * *